United States Patent [19]

McAllister et al.

[11] 4,256,694
[45] Mar. 17, 1981

[54] CARBON MONOXIDE MONITORING SYSTEM

[75] Inventors: Jerome W. McAllister; Gunter A. Kohler; Virtudes R. Lund, all of St. Paul, Minn.

[73] Assignee: Minnesota Mining and Manufacturing Company, St. Paul, Minn.

[21] Appl. No.: 912,344

[22] Filed: Jun. 5, 1978

[51] Int. Cl.³ .................... G01N 21/29; G01N 21/77; G01N 31/22
[52] U.S. Cl. ..................... 422/58; 252/408; 422/60; 422/86
[58] Field of Search ............ 422/55, 56, 58, 60, 422/86; 23/232 R; 73/28; 252/408

[56] References Cited

U.S. PATENT DOCUMENTS

| | | | |
|---|---|---|---|
| 2,408,164 | 9/1946 | Foster | 252/477 R X |
| 2,569,895 | 10/1951 | Main-Smith et al. | 23/232 R X |
| 2,961,303 | 11/1960 | Wiswesser | 422/58 X |
| 3,112,999 | 12/1963 | Grosskopf | 422/57 |
| 3,755,192 | 8/1973 | Rottig et al. | 252/477 R X |
| 3,847,552 | 11/1974 | Hobgood et al. | 23/232 R |
| 3,966,440 | 6/1976 | Roberts | 422/86 X |
| 3,985,017 | 10/1976 | Goldsmith | 23/232 R X |

OTHER PUBLICATIONS

Katz et al., "Oxidation of Carbon Monoxide in Air by Silver Permanganate", *Ind. & Eng. Chem.*, vol. 42, p. 345 (1950).

*Primary Examiner*—Arnold Turk
*Attorney, Agent, or Firm*—C. Alexander; D. M. Sell; E. T. Okubo

[57] ABSTRACT

Colorimetric indicator material comprising alumina impregnated with permanganate ion and silver ion which changes color from purple to brown in the presence of carbon monoxide is disclosed. A personal monitor containing permanganate ion and silver ion impregnated alumina which changes color completely when the carbon monoxide exposure over a given period of time exceeds a predetermined concentration is disclosed.

17 Claims, 2 Drawing Figures

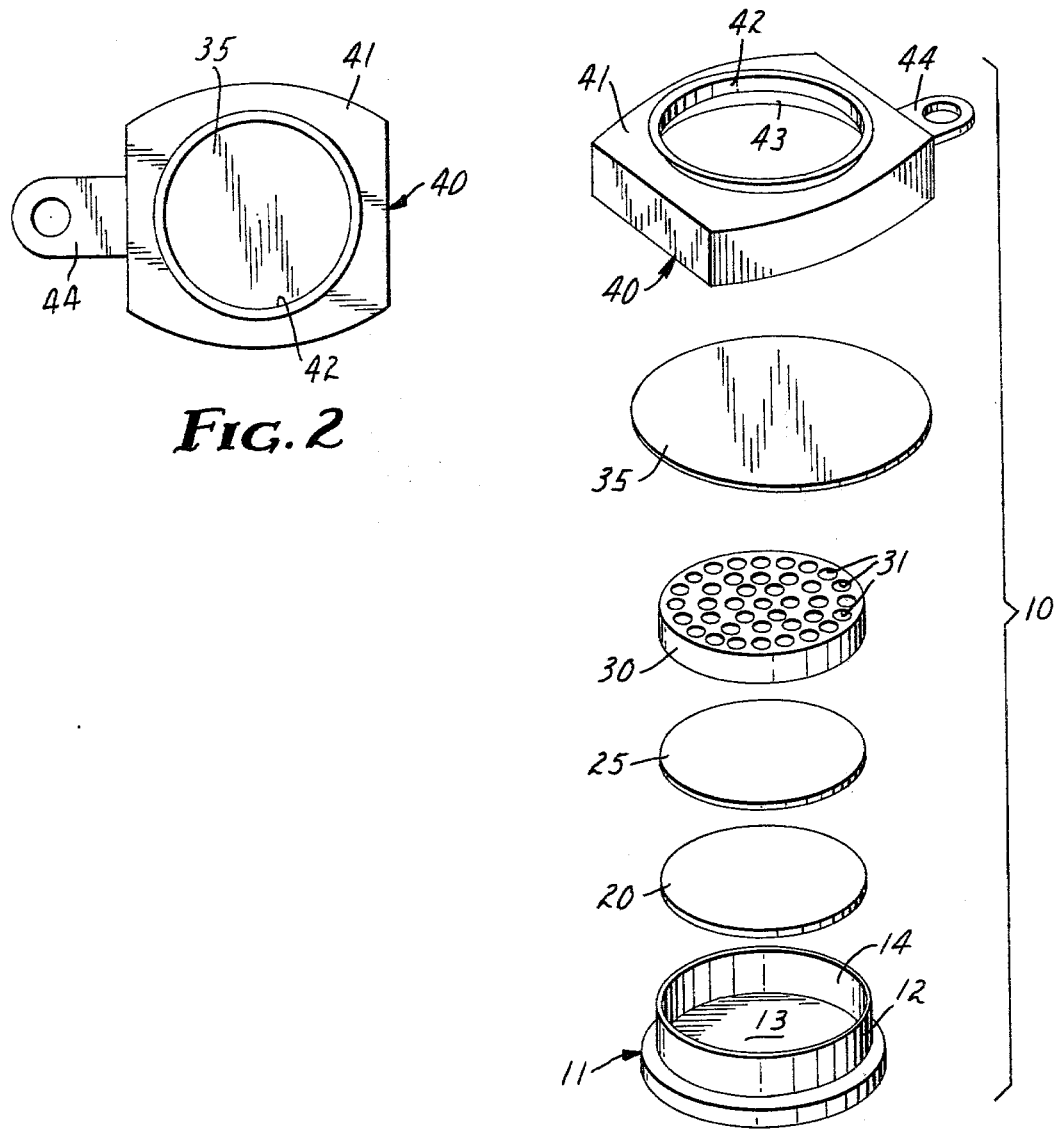

CARBON MONOXIDE MONITORING SYSTEM

BACKGROUND OF THE INVENTION

The present invention relates to a system for monitoring personal exposure to carbon monoxide. In the system of the present invention, carbon monoxide is oxidized by alumina impregnated with silver ion and permanganate ion, the oxidation resulting in the impregnated alumina changing color from purple to brown.

Commercial devices in the form of indicator tubes for monitoring personal exposure to various toxic gases or vapors are well known. An indicator tube is a glass tube containing a granular chemical and is worn by the user in a position close to his breathing zone. A pump connected to the tube pulls air from the atmosphere through the tube. The granular material reacts chemically with the toxic gas and a color change occurs. The color change progresses from the entrance to the exit of the tube as the various cross sectional layers react. At the end of any given sampling period, the length of the color change stain in the tube is proportional to the concentration of the toxic gas averaged over the sampling period.

Prior workers have reported in the literature that silver permanganate, when coated on various porous substrates, will produce materials which oxidize carbon monoxide in the ambient atmosphere. See, for example, M. Katz and S. Halpern, "Oxidation of Carbon Monoxide in Air by Silver Permanganate", *Ind. & Eng. Chem.*, Vol. 42, p. 345 (1950).

SUMMARY OF THE INVENTION

The present invention relates to a system for monitoring personal exposure to carbon monoxide and utilizes alumina impregnated with permanganate ion and silver ion as the active material in a personal monitor.

The permanganate-silver impregnated alumina is formulated by immersing the alumina in a solution of permanganate and silver, draining the excess solution, and drying under vacuum. The solution is comprised of water soluble salts of silver and permanganate with noninterfering counter ions. The resulting purple material oxidizes carbon monoxide at a rate proportional to the ratio of $Ag^+$ to $MnO_4^-$ concentrations. The oxidation reaction causes the purple material to change color from purple to brown. The impregnated alumina is utilized in a personal monitor for carbon monoxide. The monitor samples the ambient atmosphere at a diffusion controlled rate. If the atmosphere contains a predetermined concentration, say 50 ppm of carbon monoxide, the impregnated alumina will change color completely from purple to brown in a predetermined time. The rate of color change of the impregnated alumina in the monitor is independent of the relative humidity and the presence of organic vapors in the atmosphere.

The present invention provides a permanganate-silver impregnated alumina wherein the rate of carbon monoxide oxidation and hence, the rate of color change is proportional to the ratio of the silver concentration to the permanganate concentration.

The present invention also provides a personal monitor for carbon monoxide containing permanganate-silver impregnated alumina wherein the monitor samples the CO from the atmosphere at a diffusion controlled rate and the impregnated alumina reacts with the sampled CO, changing color from purple to brown at a rate proportional to the atmospheric CO concentration.

BRIEF DESCRIPTION OF THE DRAWINGS

In the accompanying schematic diagrammatic drawings which illustrate the personal monitor forming a part of the present invention:

FIG. 1 is an isometric exploded view of the personal monitor of the present invention; and FIG. 2 is a top plan view of the assembled personal monitor.

DETAILED DESCRIPTION OF THE INVENTION

The exposure of employees at their workplaces to carbon monoxide is greater than for any other chemical or physical agent. Carbon monoxide in the ambient air is commonly found in refineries, foundries, pulp mills, sintering mills, lampblack plants, formaldehyde manufacturing, arc welding, auto repair shops, traffic control operations and tunnel construction sites. Exposure to high concentrations of CO for even short periods of time can cause serious health hazards—1600 ppm of CO in the air can cause headaches, dizziness, and nausea in 20 minutes, and in two hours collapse, unconsciousness and possibly death. Exposure to low concentrations, on the order of 100 ppm, for extended periods of time can result in behavioral changes, cardiovascular damage and brain damage. Although precautions are taken to eliminate CO from the workplace air, CO can frequently be found in concentrations up to 200 ppm. The United States Government has established 50 ppm TWA for carbon monoxide as the official standard for industrial air (Federal Register, Vol. 36, No. 105, May 29, 1971). The TWA is the time-weighted average concentration for a normal 8-hour workday or 40-hour work week, to which nearly all workers may be repeatedly exposed, day after day, without adverse effect. Thus, worker health and federal regulations dictate that employers with a potential CO hazard monitor the exposure of their workers to determine if their average exposure exceeds 50 ppm.

The impregnated activated alumina of the present invention is prepared by immersing alumina in a water solution of permanganate ion and silver ion followed by draining excess solution and drying under vacuum. The alumina can be any form of porous, high surface area alumina which is referred to as activated alumina. The activated alumina can be powdered, granular, extruded or molded into shapes.

The activated alumina utilized in a preferred embodiment of a monitor of the present invention is in the form of 30 mm. diameter by 1.6 mm. thick discs which are made according to the following procedure. The discs are cut from rods made up of equal weights of two types of aluminas; RA-1, an activated alumina from the Chemical Division of Reynolds Metal Company, and A300, a partially calcined alumina hydrate from Kaiser Chemicals. RA-1 alumina is received in an 8×14 mesh distribution, but is ball milled and classified to minus 150 mesh. A300 alumina is used as received (minus 325 mesh). 100 g of RA-1 is mixed with 100 g of A300. The alumina mixture is thoroughly combined with 115 ml of a 10% hydrogen peroxide solution to form a slurry. The slurry is poured into a 30 mm.×80 mm. Whatman Extraction Thimble Cellulose Single Thickness which is contained in a glass tube. The glass tube and the contents are placed in a closed container which also contains an amount of water. The alumina slurry is cured in this closed container for 18 hours at a temperature of 90° C. After the curing period, the alumina is a solid rod 30 mm.×80 mm. of activated alumina. After removing the thimble, the rod is sawed into discs 1.6 mm thick, and the discs are heated under vacuum at 450° C. for 1 hour. The $H_2O_2$ is vaporized from the rod during the 90° C. heating step. The vaporization causes macroscopic pores to form throughout the alumina rod resulting in a molded alumina that is open to the diffusion of gases or vapors.

The activated alumina discs are then impregnated with permanganate ion and silver ion by the following general process. Water soluble salts of permanganate and silver are selected; the counter ions must be chemically non-interfering. The salts used in the preferred embodiment of a monitor of the present invention are $KMnO_4$ and $AgNO_3$. Solutions are prepared separately, then mixed together, heated to 50° C. and agitated for 5 minutes. The alumina is immersed in the 50° C. solution for one minute. Next, the alumina is removed from the solution in the case of molded discs or extruded sheets, or the mixture of alumina and solution is passed through a buchner funnel in the case of powdered or granular alumina. Powdered or granular alumina is then dried in a rotating evaporator for one hour at 60° C., with vacuum provided by an aspirator. Extruded or molded alumina is dried by placing it in a vacuum oven at 60° C. and about 20 mm mercury for 3 hours.

The kinetics of the CO oxidation by the impregnated alumina are described by the following equation:

$$-d[CO]/dt = k_1 [CO]^l [MnO_4^-]^m [Ag^+]^n,$$

where t is time in minutes,

[CO] is the gas phase CO concentration, $[MnO_4^-]$ is the surface concentration of permanganate, $[Ag^+]$ is the surface concentration of silver, $k_1$, m, n are constants.

If the CO is introduced to a sample of coated alumina and if the molar amount of permanganate and silver are constant, then the equation becomes $$-d[CO]/dt = k_2[CO]^l$$

where $k_2$ is a rate constant with units of $min^{-1}$.

The rate constant, $k_2$, is measured by employing a closed system containing a Wilks Infrared Analyzer, a glass vessel containing alumina impregnated with permanganate and silver, and a circulating pump. The system is filled to 1 atmosphere pressure with air containing 20% RH. CO is then introduced in an amount necessary to raise the system concentration to 10 ppm. The concentration as a function of time is then monitored by the Wilks Infrared Analyzer and recorded by a strip chart recorder. The data is plotted log [CO] versus time, and a straight line results which has a slope equal to $k_2$.

EXAMPLE 1

Activated alumina (RA-1 from the Chemical Division of Reynolds Metals Co.) was screened to obtain a fraction which passes U.S. Screen size 8 and is retained on U.S. Screen size 14. Samples of the alumina were impregnated from different solutions of $KMnO_4$ and $AgNO_3$. 7 grams of each sample were introduced into a closed system, and the rate constant $k_2$ was measured for each sample.

| SAMPLE | $[KMnO_4]$ moles/l | $[AgNO_3]$ moles/l | $k_2$ $min^{-1}$ |
|---|---|---|---|
| A | $1.58 \times 10^{-2}$ | $0.74 \times 10^{-2}$ | 0.0251 |
| B | $1.58 \times 10^{-2}$ | $1.48 \times 10^{-2}$ | 0.0372 |
| C | $1.58 \times 10^{-2}$ | $2.96 \times 10^{-2}$ | 0.2030 |

EXAMPLE 2

Treated alumina samples were prepared and tested exactly as described in Example 1 except that silver permanganate ($AgMnO_4$) was used in the coating solution rather than potassium permanganate.

| SAMPLE | $[AgMnO_4]$ moles/l | $[AgNO_3]$ moles/l | $k_2$ $min^{-1}$ |
|---|---|---|---|
| D | $8.8 \times 10^{-2}$ | 0 | .512 |
| E | $4.4 \times 10^{-2}$ | 0 | .314 |
| F | $3.1 \times 10^{-2}$ | 0 | .175 |
| G | $8.8 \times 10^{-2}$ | $4.0 \times 10^{-2}$ | .628 |

The data in Example 1 clearly show that for a fixed concentration of $KMnO_4$, the CO oxidation rate increases with an increase in concentration of $AgNO_3$. Since only the permanganate ion gives the alumina its characteristic purple starting color and the final brown color appears when all the permanganate ion has been consumed in the oxidation of carbon monoxide, it is now possible to produce alumina in which the color, both initial and final, is controlled by the concentration of permanganate and the rate of color change is controlled by the concentration of silver.

The data for sample points D & G in Example 2 show that for a fixed concentration of $AgMnO_4$, the CO oxidation rate increases with the addition of $AgNO_3$. Therefore, for a fixed initial and final color of $AgMnO_4$ impregnated alumina, the rate of color change can be increased by the addition of silver ion.

Examples 1 and 2 show clearly that alumina coated with either $KMnO_4$ plus $AgNO_3$ or $AgMNO_4$ plus $AgNO_3$ rapidly oxidize CO. Color values are imparted by the permanganate ion and the rate of color change for a sample of any given initial color is controlled by the concentration of silver. For alumina coated with $AgMnO_4$ only, the rate of color change can be varied by varying the $AgMnO_4$ concentration; this is demonstrated by samples D, E, and F in Example 2. However, for the $AgMnO_4$ only system, the starting color varies as the rate of color change varies.

EXAMPLE 3

Activated alumina (RA-1 from the Chemical Division of Reynolds Metal Co.) was screened to obtain a fraction which passes U.S. Screen Size 8 and is retained on U.S. Screen Size 14. Samples of the alumina were impregnated separately from various solutions of permanganate and silver salts. In each solution the concentration of permanganate ion ($MnO_4^-$) was $2.10 \times 10^{-2}$ moles/liter and the concentration of silver ion ($Ag^+$) was $4.64 \times 10^{-2}$ moles/liter. Each sample was tested by placing 10 grams in a 15 mm. diameter glass tube and flowing 5 liters/mm. of ambient air containing 50 ppm CO and 20% relative humidity through the tube. A Wilks Infrared Analyzer was used to monitor the CO concentration both upstream and downstream from the sample. The sample was tested until 50 ppm CO was measured in the downstream concentration. The data reported was (a) the time elapsed until 47.5 ppm CO was measured in the downstream air, (b) the time elapsed until the sample changed color from purple to brown as noted by visual inspection, and (c) the total moles of CO removed from the air by the sample. In addition, a MacBeth Densitometer with a red filter was used to measure the color density of each sample before and after testing.

| Impregnant Salts | Color Density Initial | Color Density Final | Total Amount CO Removed (moles × 10³) | 47.5 ppm Penetration time Minutes | Color Change Time (Minutes) |
|---|---|---|---|---|---|
| Mg(MnO₄)₂/AgNO₃ | .93 | .60 | .099 | 15 | 13 |
| Ca(MnO₄)₂/AgNO₃ | .97 | .64 | .096 | 16 | 14 |
| Zn(MnO₄)₂/AgNO₃ | .77 | .58 | .104 | 17 | 16 |
| Cd(MnO₄)₂/AgNO₃ | .84 | .55 | .092 | 15 | 13 |
| KMnO₄/AgNO₃ | .91 | .60 | .105 | 16 | 13 |
| KMnO₄/AgClO₄ | .90 | .56 | .100 | 15 | 13 |
| KMnO₄/AgF | .86 | .61 | .105 | 17 | 15 |
| KMnO₄/Ag₂SO₄ | .92 | .59 | .066 | 14 | 12 |
| Mg(MnO₄)₂/AgClO₄ | .91 | .62 | .142 | 19 | 16 |

The data in Example 3 show that oxidation of CO by permanganate-silver impregnated alumina is independent of the particular salts selected to make the impregnating solution. The salts are all water soluble, and the counter ions are all chemically non-interfering with the permanganate or silver. For a series of nine chemically different permanganate-silver impregnating solutions, the impregnated alumina shows a color change from purple to brown when exposed to 50 ppm CO. The color change is substantially the same as shown by the constancy of the initial and final color densities, and the rate of color change is the same as shown by the color change times. Also, both the extent of reaction and the rate of reaction are the same; this is demonstrated by the relative constancy of the total amount of CO removed and of the time to 47.5 ppm CO penetration, respectively. These data indicate that virtually the same colorimetric indicator material can be made by impregnating alumina with a solution of any salts of silver and permanganate provided these salts are water soluble and have chemically non-interfering counter ions.

Referring now particularly to the drawings, personal monitor 10 comprises a housing 11, activated alumina disc 20, activated alumina prefilter disc 25, diffuser plate 30, attenuating layer 35 and retainer 40. The housing 11, diffuser plate 30 and retainer 40 are injection molded of a translucent plastic such as polypropylene. The housing 11 comprises an upstanding open-ended cylindrical body portion 12, with a substantially flat end wall 13 forming a cavity 14 having a 30 mm. internal diameter, into which activated alumina disc 20 measuring 30 mm.×1.6 mm. and impregnated with silver and permanganate and weighing about 1 gram is placed. The disc 20 is viewed via the translucent end wall 13 which forms the bottom of the housing 11. On top of the permanganate-silver alumina disc 20, activated alumina prefilter disc 25 coated only with KMnO₄ is placed. Its dimensions are 30 mm.×1.6 mm. with a weight of 1 gram. Next in the array is diffuser plate 30 in the form of a disc which has a 30 mm. diameter by 5 mm. thickness with 39 equally spaced diffusion channels 31 each having a 2.5 mm. diameter. On top of the diffuser plate 30, supported at its periphery by the cylindrical body portion 12, is placed attenuating layer 35. A suitable attenuating layer material is a 1 mil thick microporous polypropylene film obtained from the Celanese Plastics Company under the trade designation Celgard 2400. The layer 35 controls diffusion such that the rate of diffusion through the plate is independent of the face velocity of the air. Finally, retainer 40 holds all the parts in place via a mechanical fit. Retainer 40 comprises a shell 41 having a central opening 42 with an internal diameter just slightly less than the internal diameter of body portion 12. Depending from shell 41 is an open-ended cylindrical member 43 having an internal diameter substantially corresponding but slightly less than the external diameter of body portion 12 so that when cylindrical member 43 is telescoped onto body portion 12, a friction fit results so that the various parts are retained together. In the embodiment illustrated in the drawings, cylindrical member 43 is formed as a stepped cylinder so that the leading edge thereof fits over the edge of end wall 13. Retainer 40 is provided at one end with an apertured tab 44 so that the monitor 10 can be affixed to the clothing of a worker by a suitable fastening device (not shown).

Permanganate-silver impregnated alumina oxidizes CO from the ambient air. Experiment has shown that it also oxidizes virtually all organic vapors from air; the only organic vapors identified which are not so oxidized are the totally halogenated vapors such as carbon tetrachloride. However, in industrial settings, CO generally coexists with a multitude of other organic vapors. It has been found that alumina impregnated with KMnO₄ reacts with the same compounds as permanganate-silver impregnated alumina except that such KMnO₄ impregnated alumina does not react at an appreciable rate with carbon monoxide. Thus, in personal monitor 10, the KMnO₄ impregnated alumina prefilter disc 25 effectively removes any organic vapor capable of being oxidized by the permanganate-silver impregnated alumina disc 20, while allowing CO to pass freely therethrough.

It is known that the rate of CO oxidation by the permanganate-silver impregnated alumina is influenced by water vapor. Thus, for a fixed concentration of carbon monoxide, the time for a complete color change increases as the water vapor content of the ambient air increases. However, since activated alumina is a desiccant material, the KMnO₄ impregnated alumina prefilter disc 25 also removes water vapor from the incoming air before it reaches the permanganate-silver impregnated alumina disc 20. Hence, in personal monitor 10, the color change time is essentially independent of the relative humidity of the air being sampled.

The monitors 10 are tested by introducing carbon monoxide into an airstream, monitoring CO concentration with a Wilks Infrared Analyzer, introducing water vapor into the airstream, monitoring the relative humidity with a wet bulb-dry bulb psychrometer, and finally allowing the airstream to flow across the entrance of the monitors. The face velocity at the monitor entrance is maintained above 9 meters per minute. During a test, the permanganate-silver impregnated alumina disc 20 is observed visually through the translucent viewing window 12. The disc 20 changes color slowly and continuously beginning with the first exposure to CO. The time interval necessary for the visible portion of the permanganate-silver disc 20 to change from purple to brown is measured.

EXAMPLE 4

Alumina discs cut from a single rod, produced in the manner hereinbefore described, were coated from a solution of $2.94 \times 10^{-2}$ moles/liter $AgNO_3$ and $1.58 \times 10^{-2}$ moles/liter $KMnO_4$. Discs from the same rod were coated from a solution of 0.316 moles/liter $KMnO_4$. Six monitors were fabricated using one disc from each batch per monitor. The monitors were tested simultaneously at 50 ppm CO and 20% relative humidity. The times necessary for complete color change from purple to brown were measured; the times were 248 mins., 258 mins., 288 min., 288 min., 276 min., and 272 mins.

EXAMPLE 5

Activated alumina (RA-1 from the Chemical Division of Reynolds Metal Co.) was ball milled and screened to obtain a fraction which passes U.S. Screen Size 40 and is retained on U.S. Screen Size 80. A portion of the alumina was impregnated from a solution of $2.94 \times 10^{-2}$ moles/liter $AgNO_3$ and $1.58 \times 10^{-2}$ moles/liter $KMnO_4$. A second portion of the alumina was impregnated from a solution of 0.316 moles/liter $KMnO_4$. Monitors were made by placing a uniform layer (about 1 g) of the $KMnO_4$-$AgNO_3$ granules on the bottom of a receptacle and a second layer (about 1 g) of the $KMnO_4$ granules thereover. Two monitors were tested at each of various concentrations of CO and the color change time was measured at each concentration. The relative humidity in all tests was 20%.

| CO Concentration (ppm) | Color Change Time (mins) |
|---|---|
| 50 | 170, 180 |
| 60 | 144, 144 |
| 100 | 96, 84 |

EXAMPLE 6

Monitors were made as described in Example 5. The monitors were used to measure the average CO concentration in an industrial setting known to have CO present. The monitors were placed in four different locations and the color of each monitor was observed as a function of time. At each location, an Ecolyzer Portable Carbon Monoxide Monitor was used to measure the CO concentration, and a strip chart recorder was used to record the Ecolyzer output as a function of time. After the tests were completed, the recorder traces were integrated to determine the time weighted average concentration.

| Monitor Number | Average CO Concentration by Ecolyzer (ppm) | Observed Color Change Time (mins) | Calculated Color Change Time (mins) |
|---|---|---|---|
| 1 | 48.6 | 184 | 181 |
| 2 | 10 | still purple @184 | 880 |
| 3 | 67 | 140 | 132 |
| 4 | 21 | still purple @140 | 418 |

The laboratory data in Example 5 show that the monitor integrates the CO concentration in a linear fashion. It shows that approximately 8800 ppm-minutes of CO is required to change the monitor from purple to brown. Using the 8800 ppm-min. value from Example 5, color change times for the monitors of Example 6 were calculated using the average concentrations obtained from the Ecolyzer measurements (column 2).

EXAMPLE 7

Alumina discs cut from a single rod were impregnated from a solution of $2.94 \times 10^{-2}$ moles/liter $AgNO_3$ and $1.58 \times 10^{-2}$ moles/liter $KMnO_4$. Discs from the same rod were impregnated from a solution of 0.316 moles/liter $KMnO_4$. Monitors were fabricated using one disc from each batch. Monitors were tested at 50 ppm CO and varying relative humidity. At 20% relative humidity, an average color change time of 225 mins. was observed; at 80% relative humidity 230 mins. was measured.

EXAMPLE 8

Alumina discs cut from a single rod were coated from a solution of $2.94 \times 10^{-2}$ moles/liter $AgNO_3$ and $1.58 \times 10^{-2}$ moles/liter $KMnO_4$. Discs from the same rod were impregnated from a solution of 0.316 moles/liter $KMnO_4$. Monitors were fabricated using one disc from each batch. Monitors were tested at 50 ppm CO and 20% relative humidity, and an average color change time of 303 minutes was observed. Monitors were tested also at 50 ppm CO, 20% relative humidity and 34 ppm ethylene, and an average color change time of 312 mins. was measured.

EXAMPLE 9

An extrudable alumina monohydrate, Catapal SB from Conoco, was used to make monitors. 180 grams of Catapal was added to 120 g of water with 0.75% $HNO_3$ and blended in a sigmoid mixer. This paste was extruded under low pressure into a 30 mm. tube, and after removal from the tube, it was air dried overnight. The rod was activated by heating at a rate of 50° C./hr. until a temperature of 600° C. was achieved. After four hours at 600° C. the rod was then cut into 1.6 mm. thick discs and impregnated from a solution of $1.47 \times 10^{-2}$ moles/liter $AgNO_3$ and $0.79 \times 10^{-2}$ moles/liter $KMnO_4$. Discs from the same rod were impregnated from a solution of 0.316 moles/liter $KMnO_4$. Monitors were fabricated using one disc from each batch. Monitors tested at 100 ppm CO and 20% relative humidity gave a color change time of 98 minutes.

EXAMPLE 10

Alumina discs cut from a single rod were impregnated from solutions of various concentrations of silver permanganate or of various concentrations of potassium permanganate and silver nitrate. For each disc the color density was measured in 8 different locations with a MacBeth Densitometer using a red filter. Discs from a second rod were impregnated from a solution of 0.316 moles/liter $KMnO_4$. Monitors were fabricated using one disc from each batch per monitor. The monitors were tested at 50 ppm CO and 20% relative humidity and the time for complete color change was noted for each monitor. The monitors were then disassembled, and the density was measured again in exactly the same manner. The data is given in the following table:

| [AgMnO4] (moles/liter) | [KMnO4] (moles/liter) | [AgNO3] (moles/liter) | Initial Color Density Average | Initial Color Density Std. Dev. | Color Change Time (mins) | Final Color Density Average | Final Color Density Std. Dev. |
|---|---|---|---|---|---|---|---|
| 8.80 × 10⁻² | 0 | 0 | 0.88 | 0.016 | 724 | 0.32 | 0.013 |
| 4.40 × 10⁻² | 0 | 0 | 0.65 | 0.033 | 400 | 0.25 | 0.013 |
| 3.08 × 10⁻² | 0 | 0 | 0.54 | 0.015 | 217 | 0.22 | 0.010 |
| 0.22 × 10⁻² | 0 | 0 | 0.14 | 0.008 | 44 | 0.06 | 0.010 |
| 0 | 1.58 × 10⁻² | 0.37 × 10⁻² | 0.67 | 0.017 | 557 | 0.30 | 0.011 |
| 0 | 1.58 × 10⁻² | 0.74 × 10⁻² | 0.68 | 0.014 | 497 | 0.31 | 0.013 |
| 0 | 1.58 × 10⁻² | 1.47 × 10⁻² | 0.67 | 0.018 | 416 | 0.29 | 0.010 |
| 0 | 1.58 × 10⁻² | 2.94 × 10⁻² | 0.67 | 0.021 | 339 | 0.30 | 0.014 |
| 0 | 1.58 × 10⁻² | 4.41 × 10⁻² | 0.66 | 0.016 | 239 | 0.31 | 0.007 |

EXAMPLE 11

Alumina discs cut from a single rod, produced in the manner hereinbefore described for the preferred embodiment, were impregnated from a solution of b $2.41 \times 10^{-2}$ moles/liter $AgClO_4$ and $0.45 \times 10^{-2}$ moles/liter $Ca(MnO_4)_2$. Discs from the same rod were coated from a solution of 0.316 moles/liter $KMnO_4$. A monitor was fabricated using one disc from each batch per monitor. The monitor was tested at 50 ppm CO and 20% relative humidity. The time necessary for complete color change from purple to brown was 165 mins.

Example 4 gives data for monitors of the preferred structure, i.e., molded alumina impregnated with a solution of potassium permanganate and silver nitrate. The average color change time is 272 minutes with a standard deviation of 16.1 minutes. Examples 5 and 9 show data for two additional forms of alumina, granular and extruded, respectively. These data show that the monitor demonstrates efficacy in laboratory testing using activated alumina in several different forms. Example 6 demonstrates efficacy under an actual use situation for monitors made from granular alumina. Examples 5 and 6 show that the monitor integrates CO concentration in a linear fashion both in laboratory and actual use situations and that actual use data are predictable from laboratory data.

Example 7 shows that the monitor demonstrates the same color change time at 20% relative humidity as it does at 80% relative humidity. Example 8 demonstrates that the monitor performs the same in the presence of other organic vapors.

Example 10 shows that for monitors made from discs impregnated with potassium permanganate and silver nitrate, the color change time decreases with increasing silver nitrate concentration at a fixed potassium permanganate concentration. For these same conditions, neither the initial color nor the final color changes with silver nitrate concentration. For monitors made from discs impregnated with silver permanganate only, the color change time decreases with decreasing silver permanganate concentration. However, under these same conditions, both the initial and final colors varied with silver permanganate concentration.

Example 11 shows that the monitor can be made from alumina discs impregnated from a solution of salts other than $KMnO_4$ and $AgNO_3$. The initial color, final color, and rate of color change are approximately the same for the $Ca(MnO_4)_2$—$AgClO_4$ system as for the $KMnO_4$—$AgNO_3$ system.

What is claimed is:

1. Colorimetric indicator material for the detection of carbon monoxide in ambient air comprising alumina having sorbed thereon a mixture containing silver ion and permanganate ion in a molar ratio of about 4:1 to about 1:4, said mixture, upon exposure to air containing carbon monoxide undergoing a color change from purple to brown at a rate proportional to the ratio of silver ion to permanganate ion in said mixture and the atmospheric CO concentration.

2. Colorimetric indicator material according to claim 1 wherein the alumina is a porous molded disc.

3. Colorimetric indicator material according to claim 1 wherein the alumina is in granular form.

4. Colorimetric indicator material according to claim 1 wherein said sorbed mixture on said alumina is the dried product of an impregnating solution containing silver ion and permanganate ion in a molar ratio of about 4:1 to about 1:4.

5. Colorimetric indicator material according to claim 4 wherein said sorbed mixture on said alumina comprises $AgNO_3$ and $KMnO_4$.

6. A device for colorimetrically monitoring personal exposure to carbon monoxide in ambient air comprising:
    a body having wall members defining a chamber having an open end;
    a colorimetric indicator material for detecting carbon monoxide located within said chamber comprising alumina having sorbed thereon a mixture containing silver ion and permanganate ion, said mixture, upon exposure to air containing carbon monoxide undergoing a color change from purple to brown at a rate proportional to the ratio of silver ion to permanganate ion in said mixture and the carbon monoxide concentration;
    a porous attenuating layer which allows passage of ambient air therethrough closing the open end of said chamber distally to and spaced apart from said indicator material to form a relatively placid layer of gas between said ambient air and said indicator material,
    whereby the amount of carbon monoxide reacting with said colorimetric indicator material is directly proportional to the atmospheric carbon monoxide concentration and is a function of diffusion through the placid layer of gas and is substantially independent of the velocity of the ambient air at the interface of the device with the ambient surroundings.

7. A device according to claim 6 additionally including a prefilter means for removing oxidizable organic vapors and water vapor from the ambient air being sampled, said prefilter being juxtaposed to said indicator material and located within said chamber proximate the open end thereof.

8. A device according to claim 7 wherein said sorbed mixture on said alumina is the dried product of an impregnating solution containing $AgNO_3$ and $KMnO_4$ in a molar ratio of about 4:1 to about 1:4.

9. A device according to claim 7 additionally including an apertured retainer member adapted for engagement with said wall members to seal said chamber about its periphery at said open end.

10. A device according to claim 9 additionally including a diffusion grating comprising a plate having a plurality of diffusion channels therein disposed upon said prefilter.

11. A device according to claim 7 wherein said colorimetric indicator material comprises alumina having sorbed thereon a mixture consisting essentially of $KMnO_4$ and $AgNO_3$, said mixture, upon exposure to air containing carbon monoxide, undergoing a color change from purple to brown at a rate proportional to the ratio of $AgNO_3$ to $KMnO_4$ concentration in said mixture.

12. A device according to claim 11 wherein said prefilter means comprises alumina having $KMnO_4$ sorbed thereon.

13. A device according to claim 7 wherein said wall members include a translucent end wall whereby the color change of said colorimetric indicator material may be viewed therethrough.

14. A device according to claim 13 wherein said colorimetric indicator is a porous molded disc.

15. A device according to claim 13 wherein said colorimetric indicator is in granular form.

16. A device according to claim 13 wherein said prefilter is a porous molded disc.

17. A device according to claim 13 wherein said prefilter is in granular form.

* * * * *

UNITED STATES PATENT AND TRADEMARK OFFICE
CERTIFICATE OF CORRECTION

PATENT NO. : 4,256,694

DATED : March 17, 1981

INVENTOR(S) : Jerome W. McAllister, Gunter A. Kohler, Virtudes R. Lund

It is certified that error appears in the above-identified patent and that said Letters Patent are hereby corrected as shown below:

Column 7, line 7, "$10^{31}$ 2" should read -- $10^{-2}$ --.

Signed and Sealed this

Sixteenth Day of June 1981

[SEAL]

Attest:

RENE D. TEGTMEYER

Attesting Officer     Acting Commissioner of Patents and Trademarks